(12) United States Patent
Liu et al.

(10) Patent No.: US 12,053,645 B2
(45) Date of Patent: Aug. 6, 2024

(54) SYSTEM AND METHOD FOR ROBUST TREATMENT PLANNING IN RADIATION THERAPY

(71) Applicant: Mayo Foundation for Medical Education and Research, Rochester, MN (US)

(72) Inventors: Wei Liu, Scottsdale, AZ (US); Jie Shan, Scottsdale, AZ (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 829 days.

(21) Appl. No.: 17/271,751

(22) PCT Filed: Aug. 28, 2019

(86) PCT No.: PCT/US2019/048491
§ 371 (c)(1),
(2) Date: Feb. 26, 2021

(87) PCT Pub. No.: WO2020/047044
PCT Pub. Date: Mar. 5, 2020

(65) Prior Publication Data
US 2021/0322788 A1    Oct. 21, 2021

Related U.S. Application Data

(60) Provisional application No. 62/725,720, filed on Aug. 31, 2018.

(51) Int. Cl.
*A61N 5/10*    (2006.01)

(52) U.S. Cl.
CPC .... *A61N 5/1031* (2013.01); *A61N 2005/1087* (2013.01)

(58) Field of Classification Search
CPC ...................... A61N 5/1031; A61N 2005/1087
See application file for complete search history.

(56) References Cited

U.S. PATENT DOCUMENTS

| 4,870,287 A | 9/1989 | Cole |
| 6,882,702 B2 | 4/2005 | Luo |

(Continued)

FOREIGN PATENT DOCUMENTS

EP        3228356 A1    10/2017

OTHER PUBLICATIONS

Albertini, F., et al. "Is it necessary to plan with safety margins for actively scanned proton therapy ?." Physics in Medicine & Biology 56.14 (2011): 4399.

(Continued)

*Primary Examiner* — Nicole M Ippolito
(74) *Attorney, Agent, or Firm* — Quarles & Brady LLP (57) ABSTRACT

Robust optimization systems and methods are provided for intensity modulated proton therapy (IMPT) that may be deployed in a clinically practical way to enable users to control the balance between nominal plan quality and plan robustness in a user-defined way. The method may include a normalized dose interval volume histogram (NDIVH)-based robust optimization, where the normalized dose interval (NDI) is calculated for each voxel considering dose variations in the face of uncertainties. It is then used to create a NDIVH. The area under this NDIVH curve may then be used to quantify plan robustness. By using normalized dose interval volume constraints (NDIVC) to control the shape of the NDIVH curves, plan robustness may be adjusted. The tradeoff between nominal plan quality and plan robustness can be modified in a user-defined way by adjusting positions of the NDIVCs on the NDIVH curves.

18 Claims, 10 Drawing Sheets

(56) References Cited

U.S. PATENT DOCUMENTS

| | | | | |
|---|---|---|---|---|
| 9,019,307 | B1* | 4/2015 | Grimm | G06T 11/206 345/629 |
| 2010/0054413 | A1* | 3/2010 | Sobering | G16H 20/40 378/65 |
| 2016/0059039 | A1 | 3/2016 | Liu | |
| 2017/0014642 | A1* | 1/2017 | An | A61N 5/1084 |
| 2019/0091487 | A1* | 3/2019 | Pal | A61N 5/1069 |

OTHER PUBLICATIONS

An, Y. et al., "Robust treatment planning with conditional value at risk chance constraints in intensity-modulated proton therapy," Medical Physics 44, 28-36 (2017).

Chen, W, et al. "Including robustness in multi-criteria optimization for intensity-modulated proton therapy." Physics in Medicine & Biology 57.3 (2012): 591.

Eley, J. G., et al. "Robustness of target dose coverage to motion uncertainties for scanned carbon ion beam tracking therapy of moving tumors." Physics in Medicine & Biology 60.4 (2015): 1717.

Fredriksson, A. et al. "Minimax optimization for handling range and setup uncertainties in proton therapy." Medical physics 38.3 (2011): 1672-1684.

Graeff, C. "Motion mitigation in scanned ion beam therapy through 4D-optimization." Physica Medica 30.5 (2014): 570-577.

Graeff, C. et al. "Motion mitigation in intensity modulated particle therapy by internal target volumes covering range changes." Medical physics 39.10 (2012): 6004-6013.

Graeff, C., et al. "A 4D-optimization concept for scanned ion beam therapy." Radiotherapy and Oncology 109.3 (2013): 419-424.

Graeff, C., et al. "Multigating, a 4D optimized beam tracking in scanned ion beam therapy." Technology in cancer research & treatment 13.6 (2014): 497-504.

International Commission on Radiation Units and Measurements. Prescribing, Recording, and Reporting Proton-Beam Therapy. Report 78, Washington DC, 2007. Abstract.

International Searching Authority. International Search Report and Written Opinion for application PCT/US2019/048491. Mailed on Dec. 12, 2019. 12 pages.

Knopf, A.-C., et al. "Adequate margin definition for scanned particle therapy in the incidence of intrafractional motion." Physics in Medicine & Biology 58.17 (2013): 6079.

Li, Y. et al. "Toward a thorough evaluation of IMPT plan sensitivity to uncertainties: Revisit the worst-case analysis with an exhaustively sampling approach," Med. Phys. 38, 3853 (2011).

Liu, W. et al. "Dosimetric benefits of robust treatment planning for intensity modulated proton therapy for base-of-skull cancers," Practical Radiation Oncology 4, 384-391 (2014).

Liu, W. et al. "Effectiveness of robust optimization in intensity-modulated proton therapy planning for head and neck cancers." Medical physics 40.5 (2013): 051711.

Liu, W. et al. "Exploratory Study of 4D versus 3D Robust Optimization in Intensity Modulated Proton Therapy for Lung Cancer," International Journal of Radiation Oncology Biology Physics 95, 523-533 (2016).

Liu, W. et al. "Exploratory study of the association of volumetric modulated arc therapy (VMAT) plan robustness with ocal failure in head and neck cancer," J Appl Clin Med Phys 18, 76-83 (2017).

Liu, W. et al. "Impact of respiratory motion on worst-case scenario optimized intensity-modulated proton therapy for ung cancers," Practical Radiation Oncology 5, e77-e86 (2015).

Liu, W. et al. "Influence of robust optimization in intensity-modulated proton therapy with different dose delivery techniques" Med. Phys. 39, 3089-4001 (2012).

Liu, W. et al. "PTV-based IMPT optimization incorporating planning risk volumes vs robust optimization," Medical Physics 40, 021709-021708 (2013).

Liu, W. et al. "Robust optimization in intensity-modulated proton therapy," Med. Phys. 39, 1079-1091 (2012).

Liu, W. et al. "Robustness quantification methods comparison in volumetric modulated arc therapy to treat head and neck cancer," Practical Radiation Oncology 6, E269-E275 (2016).

Lomax, A. J., et al. "The clinical potential of intensity modulated proton therapy." Zeitschrift für Medizinische Physik 14.3 (2004): 147-152.

Lowe, M., et al. "Incorporating the effect of fractionation in the evaluation of proton plan robustness to setup errors." Physics in Medicine & Biology 61.1 (2015): 413.

Mcgowan, S. E., et al. "Defining robustness protocols: a method to include and evaluate robustness in clinical plans." Physics in Medicine & Biology 60.7 (2015): 2671.

Meza, J. C., et al. "OPT++ An object-oriented toolkit for nonlinear optimization." ACM Transactions on Mathematical Software (TOMS) 33.2 (2007): 12-es.

Nocedal, J.. "Updating quasi-Newton matrices with limited storage." Mathematics of computation 35.151 (1980): 773-782.

Park, P. C., et al. "Statistical assessment of proton treatment plans under setup and range uncertainties." International Journal of Radiation Oncology* Biology* Physics 86.5 (2013): 1007-1013.

Perko, Z. et al "Fast and accurate sensitivity analysis of IMPT treatment plans using Polynomial Chaos Expansion," Physics in Medicine and Biology 61, 4646-4664 (2016).

Pflugfelder, D., et al. "Worst case optimization: a method to account for uncertainties in the optimization of Intensity modulated proton therapy." Physics in Medicine & Biology 53.6 (2008): 1689.

Quan, E. M., et al. "Preliminary evaluation of multifield and single-field optimization for the treatment planning of spot-scanning proton therapy of head and neck cancer." Medical physics 40.8 (2013): 081709.

Raystation Laboratories. "RayStation Product Brochure," edited by R. Laboratories (2018). 15 pages.

Rietzel, E. et al. "Respiratory motion management in particle therapy." Medical physics 37.2 (2010): 449-460.

Sobotta, B., et al. "Accelerated evaluation of the robustness of treatment plans against geometric uncertainties by Gaussian processes." Physics in Medicine & Biology 57.23 (2012): 8023.

Stuschke, M., et al. "Potentials of robust intensity modulated scanning proton plans for locally advanced lung cancer in comparison to intensity modulated photon plans." Radiotherapy and Oncology 104.1 (2012): 45-51.

Trofimov, A., et al. "Evaluation of dosimetric gain and uncertainties in proton therapy delivery with scanned pencil beam in treatment of base-of-skull and spinal tumors." International Journal of Radiation Oncology, Biology, Physics 78.3 (2010): S133-S134.

Unkelbach, J., et al. "Accounting for range uncertainties in the optimization of intensity modulated proton therapy," Physics in Medicine and Biology 52, 2755-2773 (2007).

Unkelbach, J., et al. "Reducing the sensitivity of IMPT treatment plans to setup errors and range uncertainties via probabilistic treatment planning." Medical physics 36.1 (2009): 149-163.

Varian Medical Systems. "Eclipse Treatment Planning System Feature Sheet," (2015). 4 pages.

Wu, J., et al. "520 Estimation of dose constraints using biologically-normalized dose-volume histogram (BN-DVH) for hypofractionated radiotherapy in the treatment of prostate cancer." EJC Supplements 5.1 (2003): S158.

Wu, Q. et al. "Algorithms and functionality of an intensity modulated radiotherapy optimization system." Medical physics 27.4 (2000): 701-711.

* cited by examiner

SYSTEM AND METHOD FOR ROBUST TREATMENT PLANNING IN RADIATION THERAPY

CROSS-REFERENCE TO RELATED APPLICATIONS

This application is a 371 U.S. National Phase application of PCT/US2019/048491, filed Aug. 28, 2019, which claims the benefit of U.S. Provisional Patent Application Ser. No. 62/725,720 filed on Aug. 31, 2018 and entitled "System and Method for Robust Treatment Planning in Radiation Therapy," which is incorporated herein by reference as if set forth in its entirety for all purposes.

STATEMENT REGARDING FEDERALLY SPONSORED RESEARCH

This invention was made with government support under CA168984 awarded by the National Institutes of Health. The government has certain rights in the invention.

BACKGROUND

Intensity-modulated proton therapy (IMPT) is unique in delivering tumoricidal dose with better conformality to target volumes and sparing of adjacent healthy tissue than conventional radiotherapy (photons or electrons). The energy deposited is more concentrated at the distal end of proton beams within the Bragg Peak. However, the sharp gradient of dose distribution of proton beams makes proton therapy more sensitive to patient setup and range uncertainties. Range uncertainties arise from multiple sources, such as computed tomographic (CT) number uncertainty, tumor shrinkage, patient weight change, and uncertainty associated with the conversion of CT numbers to proton stopping powers. Appreciable degradation of the delivered dose distributions may also occur from setup uncertainties that are due to misalignment of beams and patient motion.

There are a number of ways to address these uncertainties in the process of treatment planning. The traditional method used in photon therapy is to adopt additional margins to clinical target volume (CTV) to form planning target volume (PTV) to ensure the dose coverage of the CTV. However, this method does not take into account the changes along the proton trajectory, and tends either to overestimate the effect of uncertainties and potentially irradiate more normal tissues or to underestimate the effect of uncertainties and underdose the target.

Various robustness quantification methods to assess plan robustness have been developed. For example, the dose volume histogram (DVH) band method has been used in Eclipse (Varian Medical Systems, Palo Alto, CA) and RayStation (RaySearch Laboratories, Stockholm, Sweden) and is well received in proton therapy community. In a previous study, the concepts of the error bar and the error bar volume histogram are introduced to quantify the extent of plan robustness and have been shown to be an effective way for robustness quantification.

Some methods to account for uncertainty consider uncertainties in the optimization procedure. They can be performed in different ways such as the probabilistic robust optimization method, the objective-wise min-max robust optimization method, or the voxel-wise worst-case robust optimization method. In the voxel-wise worst-case robust optimization method, the uncertainties are represented by a number of scenarios with setup and range uncertainty. For each voxel, multiple doses are calculated corresponding to uncertainty scenarios to form the worst-case dose distribution, which is used in the optimization. In this way, the resulting plan is expected to meet the clinical requirements under less extreme scenarios. Voxel-wise worst-case robust optimization had been shown to be effective in achieving robust IMPT plans. However, the method cannot efficiently balance between plan robustness and nominal plan quality. The penalty weight of plan robustness term in the objective function denotes the importance of plan robustness in a mathematical context; therefore, it can be altered to change robustness of the resulting plan. However, the quantitative relationship between the penalty weight and the robustness of the resulting plan is not clear, varies among different cases, and can hardly be apprehended in clinical practice due to extensive computation requirements and lengthy processing times. This weakness is shared with other robust optimization methods such as probabilistic robust optimization and objective-wise min-max robust optimization.

A conditional value at risk chance constraints robust optimization method based on linear programming has also been proposed recently to control plan robustness. However, it can constrain only the tail mean dose value and the slow computing speed makes it impractical for clinic use. In addition, the use of linear programming makes it hard to be integrated in some commercial treatment planning systems such as Varian Eclipse™.

IMPT has a much larger number of optimization variables than intensity-modulated radiation therapy (IMRT) due to the additional dimension of particle energies, therefore usually requiring much longer computation time and optimization time compared to IMRT. Intensity-Modulated Proton Therapy (IMPT) is sensitive to patient setup and range uncertainties. Multiple robust optimization methods have been developed to mitigate the impact of these uncertainties, but a challenge remains with a clinically practical way to enable users to control the balance between nominal plan quality and plan robustness.

SUMMARY OF THE DISCLOSURE

The present disclosure addresses the aforementioned drawbacks by providing a robust optimization method in IMPT that may be deployed in a clinically practical way to enable users to control the balance between nominal plan quality and plan robustness, which may be performed in a user-defined way. With the uncertainties considered, each voxel might have multiple doses, each corresponding to a different uncertainty scenario. In one configuration, the method includes a radiotherapy plan optimization method where a normalized dose interval (NDI) is calculated as the full dose range variation divided by the maximum dose in all uncertainty scenarios for each voxel (NDI=[max−min dose]/max dose), which was then used to calculate the Normalized Dose Interval Volume Histogram (NDIVH) curves. The area under this NDIVH curve may then be used to quantify plan robustness, and the tradeoff between nominal plan quality and plan robustness can be adjusted by applying a Normalized Dose Interval Volume Constraint to the corresponding structures, such as both normal organs and targets, in treatment planning.

In one configuration, a method is provided for balancing radiation therapy plan robustness and nominal plan quality (without any uncertainties considered). The method includes calculating normalized dose interval for a plurality of voxels in at least one normal tissue region of interest (ROI) and at least one target ROI in a subject. A normalized dose interval volume histogram (NDIVH) may be generated using the normalized dose interval for the plurality of voxels in the at least one normal tissue ROI and the at least one target ROI in the subject and an area under the normalized dose volume histogram may be measured to determine plan robustness for the plan. The method may also include creating the radiotherapy plan using the NDIVH-based robust optimization.

In some configurations, the method includes controlling the shape of the dose interval volume histogram using the normalized dose intervals. The normalized dose intervals (NDI) may be determined by: NDI=(Dmax−Dmin)/Dmax, where Dmax represents the maximum dose, and Dmin represents the minimum dose among possible doses corresponding to different setup and range uncertainty scenarios for the plurality of voxels in the at least one normal tissue ROI and the at least one target ROI in the subject. In some configurations, the NDI are a 3D distribution in the subject.

In some configurations, an objective function may be minimized that incorporates the plan quality and the plan robustness to generate the radiotherapy plan. The objective function may incorporate the plan quality and the plan robustness to generate the radiotherapy plan using the normalized dose interval. Creating the radiotherapy plan may include adjusting a position of the normalized dose interval in the normalized dose interval volume histogram to balance between nominal plan quality and plan robustness. In some configurations, a dose volume histogram may be generated prior to generating a normalized dose interval volume histogram In some configurations, the constraints may include a threshold for plan robustness, a threshold for plan quality including target dose coverage, target dose homogeneity, normal tissue protection value, patient setup uncertainty value, proton beam range uncertainty value, or a combination thereof.

In one configuration, a system is provided for balancing radiation therapy plan robustness and nominal plan quality. The system includes a computer system configured to: i) determine, or set up, constraints for a radiotherapy plan quality; ii) calculate normalized dose interval for a plurality of voxels in at least one normal tissue region of interest (ROI) and at least one target ROI in a subject; iii) generate a normalized dose interval volume histogram using the normalized dose interval for the plurality of voxels in the normal tissue ROI and the target ROI in the subject; iv) measure an area under the normalized dose volume histogram (NDIVH) to determine plan robustness for the plan; and v) create the radiotherapy plan based on NDIVH.

In some configurations, the system includes controlling the shape of the dose interval volume histogram using the normalized dose intervals. The normalized dose intervals (NDI) may be determined by: NDI=(Dmax−Dmin)/Dmax, where Dmax represents the maximum dose, and Dmin represents the minimum dose among possible doses corresponding to different setup and range uncertainty scenarios for the plurality of voxels in the at least one normal tissue ROI and the at least one target ROI in the subject. In some configurations, the NDI are a 3D distribution in the subject.

In some configurations, the computer system may be configured to minimize an objective function that incorporates the plan quality and the plan robustness to generate the radiotherapy plan. The objective function may incorporate the plan quality and the plan robustness to generate the radiotherapy plan using the normalized dose interval. Creating the radiotherapy plan may include adjusting a position of the normalized dose interval in the normalized dose interval volume histogram to balance between nominal plan quality and plan robustness. In some configurations, a dose volume histogram may be generated prior to generating a normalized dose interval volume histogram In some configurations of the system, the constraints may include a threshold for plan robustness, a threshold for plan quality including target dose coverage, target dose homogeneity, normal tissue protection value, patient setup uncertainty value, proton beam range uncertainty value, or a combination thereof.

The foregoing and other aspects and advantages of the present disclosure will appear from the following description. In the description, reference is made to the accompanying drawings that form a part hereof, and in which is shown by way of illustration a preferred embodiment. This embodiment does not necessarily represent the full scope of the invention, however, and reference is therefore made to the claims and herein for interpreting the scope of the invention.

DETAILED DESCRIPTION

The system and method for NDIVH-based robust optimization provides robust optimization in IMPT and in a clinically practical way to enable users to control the balance between nominal plan quality and plan robustness that may be performed in a user-defined way.

In one configuration, a number of dose distributions may be calculated to account for patient setup and proton beam range uncertainties accordingly. For each voxel, the normalized dose interval (NDI) may be defined as the full variation of the doses in those uncertainty scenarios normalized by the maximum dose:

$$NDI = \frac{D_M - D_m}{D_M} \quad (1)$$

where $D_M$ is the maximum dose, and $D_m$ is the minimum dose. The Normalized Dose Interval Volume Histogram (NDIVH) curves may then be calculated following the similar statistical analysis and framework as the dose volume histogram (DVH) with the vertical axis indicating the normalized volume of a particular structure, and the horizontal axis indicated the normalized dose interval (i.e., dose variation due to uncertainties) within a particular structure.

Figure 2:
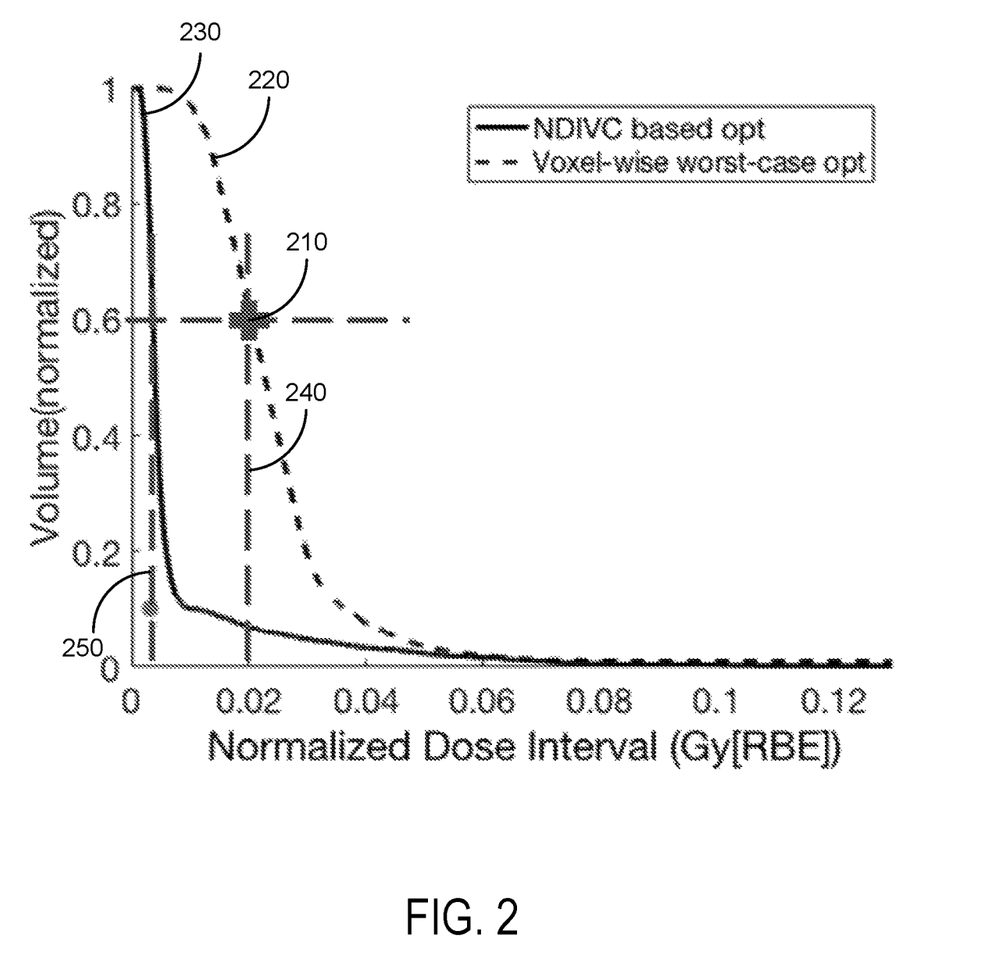
FIG. 2 is a graph showing non-limiting examples of normalized dose interval volume histogram (NDIVH) curves from two optimization methods.

Referring to FIG. 2, a typical example NDIVH is shown. The areas under the NDIVH curves may be used to quantify plan robustness. The worst-case doses are not calculated, but rather normalized dose-intervals are calculated. A Normalized Dose Interval Volume Constraint (NDIVC) may be incorporated to specify the desired robustness. Users can explore the tradeoff between nominal plan quality and plan robustness in a user-defined way by adjusting the position of NDIVCs in the NDIVH curves. In another configuration, the plan robustness may be controlled by modifying the shapes of the NDIVH curves via NDIVC, thereby balancing nominal plan quality and plan robustness in a user-defined way.

The area under the NDIVH curve (AUC) calculates a numerical index summarizing plan robustness in a manner analogous to the equivalent uniform dose summarizing a DVH; a smaller AUC value indicates better plan robustness. This numerical value can be used in a statistical study, such as a student's t-test, to compare plan robustness between two competing treatment planning methods. In another configuration, the DVH band method may also be used with the band width at $D_{95\%}$ of CTV to indicate the plan robustness.

In one configuration, the dose interval may be calculated for each voxel and normalized by the maximum dose per voxel: $NDI=(D_{max}-D_{min})/D_{max}$, thus forming a 3D distribution of NDI. The DVH may be generated and a similar statistical analysis as discussed above may be used to form the NDI volume histogram (NDIVH).

Normalization may be used in the plan robustness quantification and NDIVH-based robust optimization in order to account for the same dose variation indicating different plan robustness in the face of uncertainties for voxels with different nominal doses. For example, given the same dose variation of 5 Gy[RBE], plan robustness is good for a voxel with the nominal dose of 60 Gy[RBE] (8.3% variation of the nominal dose), while it is not good for a voxel with the nominal dose of 5 Gy[RBE] (100% variation of the nominal dose). Normalization of the dose variation may be important to show the effect of the dose variation due to the uncertainties. After normalization, it may be more effective for users to shape the NDIVH curves (thus controlling plan robustness) in NDIVC-based robust optimization.

When a dose volume constraint (DVC) is used to control the nominal plan quality, adjustment can be made to: (1) the weights of DVCs terms and/or (2) the position of DVCs in the dose volume histogram (DVH) curves. And the latter one is usually more effective and more clinically meaningful than the approach of adjusting the weight of the DVC term in the objective function in controlling nominal plan quality. In the DVC method, the physical meaning of the parameters of the DVC parameters dose value and volume, may be understood by the treatment planner and the clinical experience of physicians can be efficiently adopted in creating the DVCs. This enables controlling the plan quality in a user-defined way. The weights for the normalized dose interval (NDI) can be adjusted in the penalty term to explore the tradeoff between nominal plan quality and plan robustness, but it may be more effective to adjust the position of NDIVCs in the normalized dose interval volume histograms (NDIVH) curves to explore the tradeoff between nominal plan quality and plan robustness compared to simply adjusting the weight of the NDIVC term in the objective function. By assigning a smaller NDI value of a NDIVC constraint point, we can generate a more robust plan at the cost of nominal plan quality In some configurations, nominal plan quality may be improved by sacrificing plan robustness in the face of uncertainties or vice versa. The balance between nominal plan quality and plan robustness may be dependent on what NDIVC is used in the optimization (or may be dependent on the varying patient-specific treatment priorities). If a more robust plan is desired, a more stringent NDIVC may be used to achieve that. The applied NDVIC may be loosed to get a less robust (but better nominal plan quality) plan, if needed. One previous method proposed to use a penalty term to control the relative importance of the worst-case dose distribution-related objective function term to the nominal dose distribution-related objective function term. This previous method cannot overcome the challenge that it does not balance between plan robustness and nominal plan quality in a user-defined way. The penalty weight of the plan robustness term in the objective function may be overshadowed in a mathematical context. The quantitative relationship between the penalty weight and the robustness of the resultant plan is not clear, and can vary based on various clinical scenarios; the importance of this in the IMPT practice is still to be determined. This unclear relationship will result in more "try and error" iterations at some situation in clinical practice where a certain amount of robustness is desired. The process is very time-consuming. This weakness is commonly shared with other robust optimization methods.

Figure 1A:
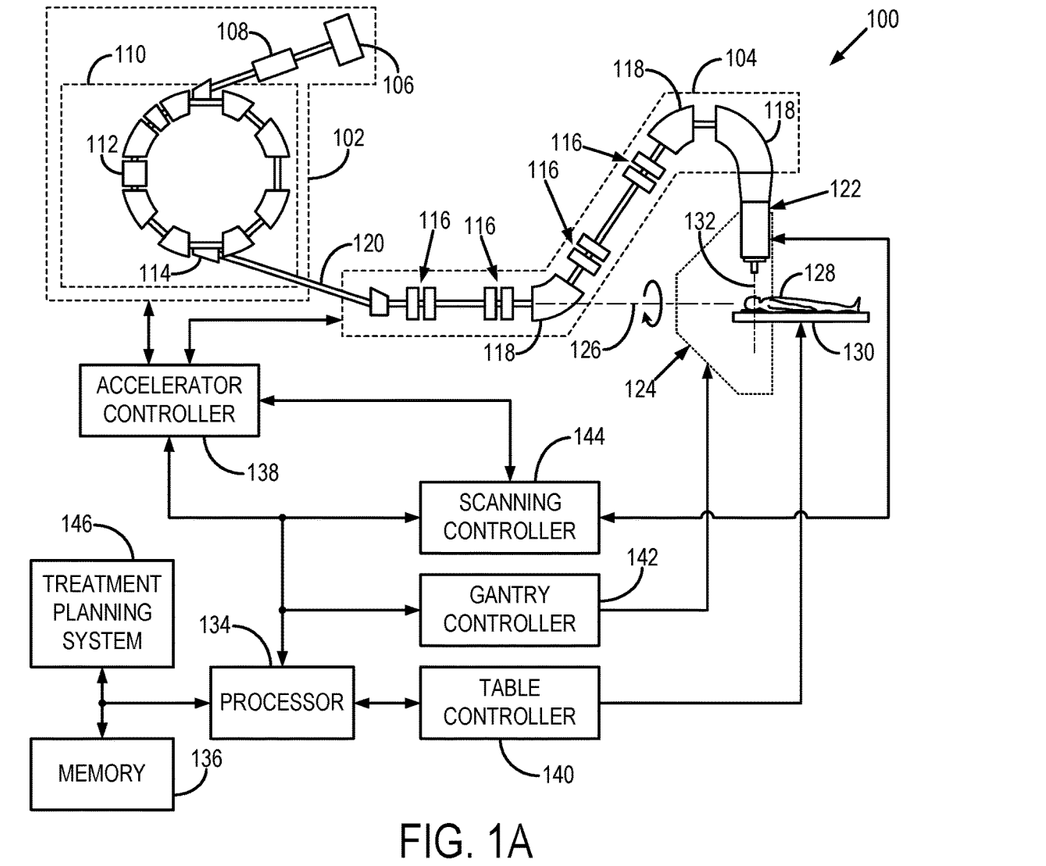
FIG. 1A is a block diagram of a non-limiting example hadron therapy system, such as a proton therapy system.
Figure 1B:
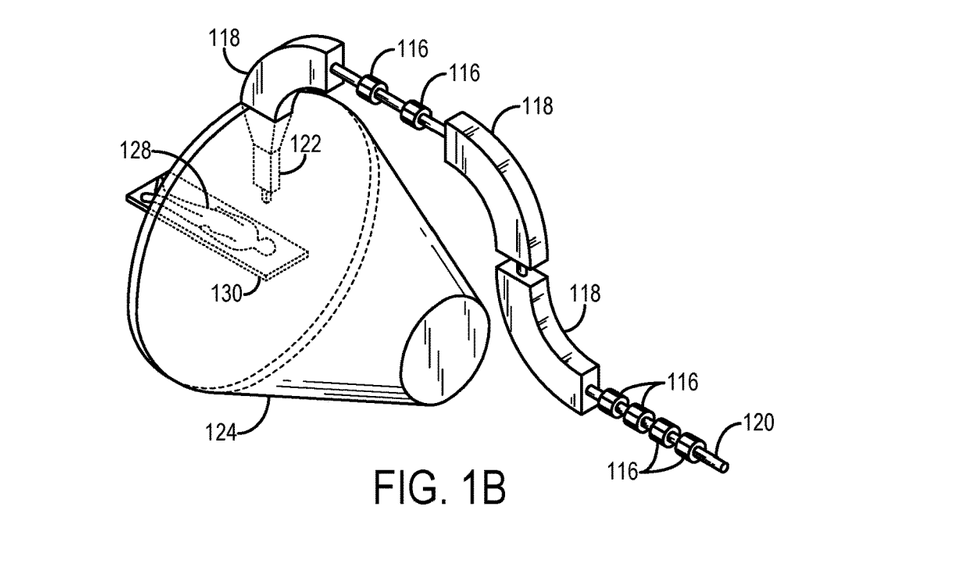
FIG. 1B is a perspective view of deflection optics coupled to a rotatable gantry, which both form a part of a non-limiting example hadron therapy system, such as the hadron therapy system of FIG. 1A.

Referring now to FIGS. 1A and 1B, an exemplary hadron therapy system 100, such as, for example, a proton beam therapy system, is illustrated. Exemplary hadrons for use with a hadron therapy system include protons, neutrons, and atoms or molecules containing such particles. For example, hadron therapy may include proton therapy, heavy ion therapy, and neutron therapy. An exemplary hadron therapy system 100 generally includes a charged particle generating system 102 and a beam transport system 104. By way of example, the charged particle generating system 102 may include a synchrotron; however, in other configurations the charged particle generating system 102 may include a cyclotron, or for some neutron therapy systems, the charged particle generating system 102 may include a linear accelerator (linac) configured to operate as a deuterium-tritium ("D-T") neutron generator. An exemplary proton beam treatment system is more fully disclosed in U.S. Pat. No. 4,870,287, which is hereby incorporated by reference in its entirety.

The charged particle beam generating unit 102 includes an ion source 106; an injector 108, such as a linac; and an accelerator 110, such as a synchrotron. The accelerator 110 includes at least one radio frequency ("RF") acceleration cavity 112. Exemplary RF acceleration cavities may include an RF applying electrode that is disposed on the circulating orbit of the accelerator 110 and an RF power source that is in electrical communication with the RF applying electrode by way of a switch.

Ions generated in the ion source 106, such as hydrogen ions (protons) or carbon ions, are accelerated by the injector 108 to form an ion beam that is injected into the accelerator 110. The accelerator 110 provides energy to the injected ion beam by way of the acceleration cavity 112, where RF energy is applied to the ion beam. In the case of a synchrotron, quadropole and dipole magnets are used to steer the ion beam about the accelerator 110 a number of times so that the ion beam repeatedly passes through the acceleration cavity 112. After the energy of the ion beam traveling in the accelerator 110 has reached a preselected, desired energy level, such as 100-200 mega-electron volts ("MeV"), the ion beam is extracted from the accelerator 110 through an extraction deflector 114. Extraction may occur by way of bumping, or kicking, the ion beam to an outer trajectory so that it passes through a septum, or by way of resonance extraction.

The beam transport system 104 includes a plurality of focusing magnets 116 and steering magnets 118. Exemplary focusing magnets 116 include quadropole magnets, and exemplary steering magnets 118 include dipole magnets. The focusing and steering magnets 116, 118 are used to contain the ion beam in an evacuated beam transport tube 120 and to deliver the ion beam to a beam delivery device 122 that is situated in a treatment room. The beam delivery device 122 is coupled to a rotatable gantry 124 so that the beam delivery device 122 may be rotated about an axis of rotation 126 to delivery therapeutic radiation to a patient 128 positioned on a patient table 130. The rotatable gantry 124 supports the beam delivery device 122 and deflection optics, including focusing and steering magnets 116, 118, that form a part of the beam transport system 104. These deflection optics rotate about the rotation axis 126 along with the beam delivery device 122. Rotation of the rotatable gantry 124 may be provided, for example, by a motor (not shown in FIGS. 1A and 1B). In some configurations, the accelerator 110 provides an ion beam to a plurality of beam delivery devices located in different treatment rooms. In such configurations, the beam transport system 104 may connect to a series of switchyards that may include an array of dipole bending magnets that deflect the ion beam to any one of a plurality of deflection optics that each lead to a respective beam delivery device in the respective treatment room.

The beam delivery device 122 is designed to deliver precise dose distributions to a target volume within a patient. In general, an exemplary beam delivery device 122 includes components that may either modify or monitor specific properties of an ion beam in accordance with a treatment plan. The beam delivery device 122 may, for example, include a device to spread or otherwise modify the ion beam position and profile, a dispersive element to modify the ion beam energy, and a plurality of beam sensors to monitor such properties. For example, scanning electromagnets may be used to scan the ion beam in orthogonal directions in a plane that is perpendicular to a beam axis 132.

The hadron therapy system 100 is controlled by a central controller that includes a processor 134 and a memory 136 in communication with the processor 134. An accelerator controller 138 is in communication with the processor 134 and is configured to control operational parameters of the charged particle generating system 102, including the accelerator 110, and the beam transport system 104. A table controller 140 is in communication with the processor 134 and is configured to control the position of the patient table 130. A gantry controller 142 is also in communication with the processor 134 and is configured to control the rotation of the rotatable gantry 124. A scanning controller 144 is also in communication with the processor and is configured to control the beam delivery device 122. The memory 136 may store a treatment plan prescribed by a treatment planning system 146 that is in communication with the processor 134 and the memory 136, in addition to control parameters to be delivered to the accelerator controller 138, the table controller 140, the gantry controller 142, and the scanning controller 144. The memory 136 may also store relevant patient information that may be beneficially utilized during a treatment session.

Before the ion beam is provided to the patient 128, the patient 128 is positioned so that the beam axis 132 intersects a treatment volume in accordance with a treatment plan prescribed by a treatment planning system 146 that is in communication with the processor 134. The patient 128 is positioned by way of moving the patient table 130 into the appropriate position. The patient table 130 position is controlled by the table controller 140, which receives instructions from the processor 134 to control the position of the patient table 130. The rotatable gantry 124 is then rotated to a position dictated by the treatment plan so that the ion beam will be provided to the appropriate treatment location in the patient 128. The rotatable gantry 124 is controlled by the gantry controller 142, which receives instructions from the processor 134 to rotate the rotatable gantry 124 to the appropriate position. As indicated above, the position of the ion beam within a plane perpendicular to the beam axis 132 may be changed by the beam delivery device 122. The beam delivery device 122 is instructed to change this scan position of the ion beam by the scanning controller 144, which receives instruction from the processor 134. For example, the scanning controller 144 may control scanning electromagnets located in the beam delivery device 122 to change the scan position of the ion beam.

There are multiple ways to access plan robustness, such as the conventional DVH band width and the worst-case analysis methods. However, the information conveyed depends on the chosen DVH parameter. For example, when comparing two plans in terms of plan robustness, the comparison between two DVH band widths at $D_{5\%}$ of the target and the comparison between two DVH band widths at $D_{95\%}$ of the target could sometimes give conflicting information. Furthermore, it may be difficult to use these methods to indicate plan robustness in a statistical study across multiple cases due to the same reason. Therefore, in clinical practice, a single, overall numerical value is preferred to represent plan robustness. In some configurations, a numerical value (i.e., the area under the NDIVH curve) can be derived from the NDIVH method and can be used to indicate plan robustness.

Referring to FIG. 2, a point on a typical NDIVH curve (dash line) 220 is indicated by cross 210. This point indicates that 60% of the selected structure, or target, has the NDI (e.g., dose variation due to uncertainties) of at least 0.02.

This gives a straightforward and quantitative idea how the dose variation is distributed within the selected structure. Using the normalized dose interval volume constraint (indicated by the line 250, in which 60% of the selected structure now has the NDI of at least 0.004), the dash line NDIVH curve 220 can be changed to the solid line NDIVH 230. This results in a more robust plan (by comparing the AUC under solid NDIVH curve 230 and the AUC under dashed NDIVH curve 220).

Dose volume constraints (DVCs) used in the radiation therapy treatment planning are effective in controlling the shape of the DVH curves and, therefore, effectively control the plan quality of the resulting radiotherapy plans. In one configuration, the normalized dose interval volume constraints (NDIVC) are used to control the shape of the NDIVH curves and thus effectively control the plan robustness of radiotherapy plans:

$$F_{NDIVC}(\vec{\omega}) = \sum_{i \in CTV} p_{CTV\_nominal}(D_i^{[nominal]} - D_{0,CTV})^2 + \qquad (2)$$
$$\underline{\sum_{i \in CTV} p_{CTV\_robust} H(NDI_2 - NDI_i) H(NDI_i - NDI_1)(NDI_i - NDI_1)^2} + \ldots, + \sum_{i \in OARs} p_{OARs} \cdot H(D_{i,max} - D_{0,OARs})(D_{i,max} - D_{0,OARs})^2$$

Where the first term in eq. 2 represents the nominal plan quality of targets; the second term, which has been underlined, represents the plan robustness of target, while the third term represents the protection of normal tissues. The gradient of the above objective function can be formulated as follows:

$$\frac{\partial F_{NDIVC}}{\partial \omega_j} = \sum_{i \in CTV} p_{CTV\_nominal} 4(D_i^{[nominal]} - D_{0,CTV}) k_{i,j}^{[nominal]} \omega_j + \qquad (3)$$
$$\sum_{i \in CTV\_constraint} p_{CTV_{robust}} 4(NDI_i - NDI_1) \frac{\left( \frac{(1 - NDI_i)}{k_{i,j}^{m_{i,max}} - k_{i,j}^{m_{i,min}}} \right)}{D_{i,max}} \omega_j +$$
$$\sum_{i \in OARs} p_{OARs} \cdot H(D_{i,max} - D_{0,OARs}) 4(D_{i,max} - D_{0,OARs}) k_{i,j}^{m_{i,max}} \omega_j$$

In eq. (2) and (3), $F_{NDIVC}$ is an objective function value.

$$\frac{\partial F_{NDIVC}}{\partial \omega_j}$$

is the first order derivative of the objective function. $D_i^{[nominal]}$ is the dose for voxel i in the nominal scenario without any uncertainty considered. CTV_constraint is the group of voxels: $\{i | i \in CTV$ and $H(NDI_2 - NDI_i) H(NDI_i - NDI_1) > 0\}$ which varies from iteration to iteration. [nominal] is the index of nominal scenario (0 in some examples). $m_{i,max}$ and $m_{i,min}$ are the indices of uncertainty scenarios for voxel i to have maximum dose and minimum dose among all doses per voxel corresponding to different uncertainty scenarios, which may vary from voxel to voxel and from iteration to iteration.

In some configurations, the DVCs and the NDIVC may be implemented as "soft constraints" in the objective function. Usually, a trial-and-error process is needed to achieve a clinically acceptable plan. In some difficult cases, one constraint can never be met unless other objectives are sacrificed. By using soft constraints in some configurations, the objectives may be met by an adjustment to one or more of the constraints themselves, and thus eliminating the need to entirely sacrifice an objective.

Figure 3:
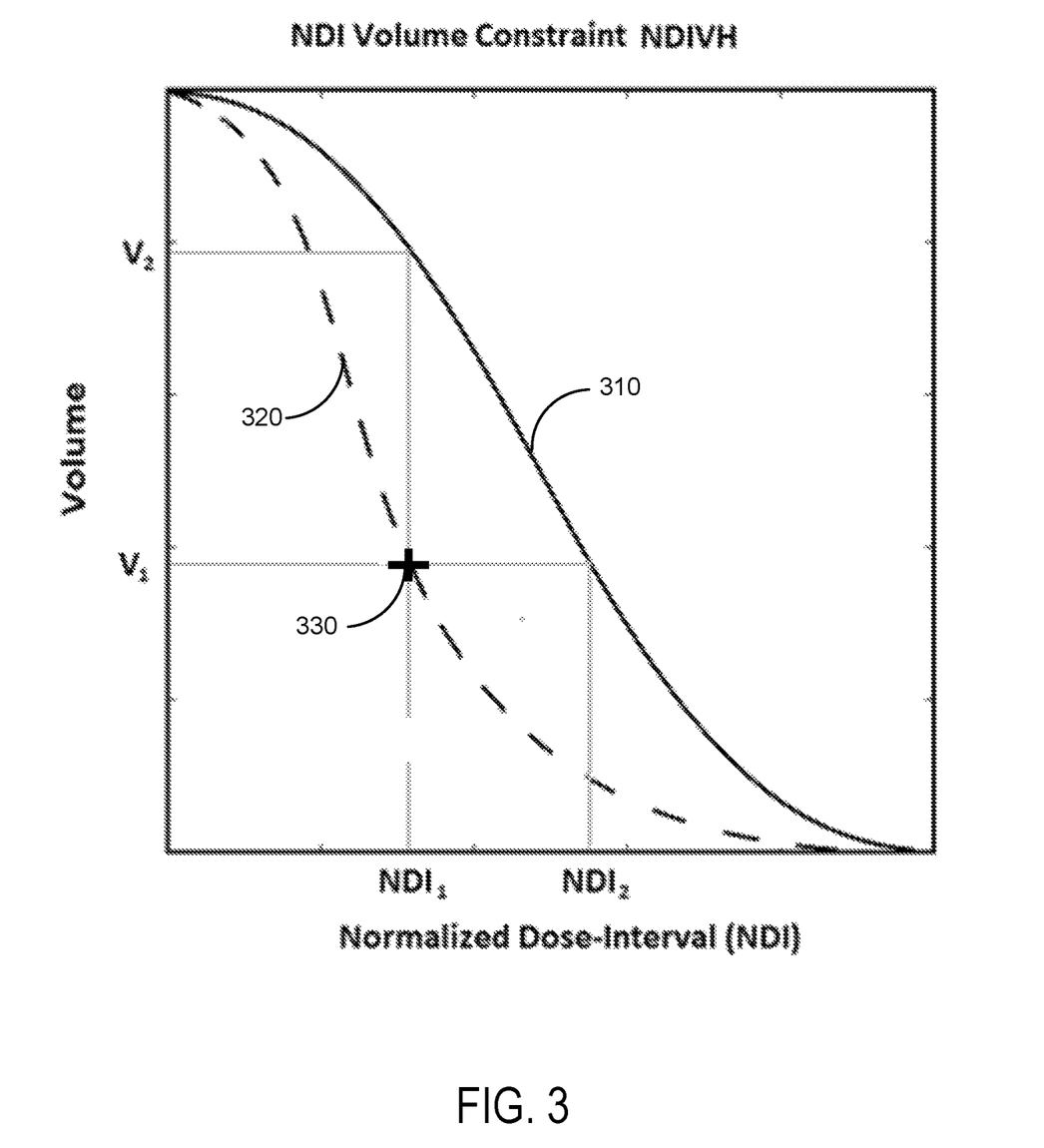
FIG. 3 is a graph showing a non-limiting example of a normalized dose interval volume constraint to balance nominal plan quality and plan robustness.

Referring to FIG. 3, one configuration for implementing an NDIVC in the objective function with "soft constraints" is shown. A NDIVH curve 310 may be changed to a desired NDIVH curve 320. NDIVC point 330 indicates what the desired $NDI_1$ and $V_1$ are on the desired NDIVH curve. The NDIVCs to limit the hot spots in the NDIVH curves can be specified as: $V(>NDI_1) < V_1$ i.e., the volume receiving NDI greater than $NDI_1$ should be less than $V_1$. Another NDI value $NDI_2$ may be derived so that in the current NDIVH, $V(NDI_2) = V_1$. In some configurations, only voxels with NDI values between $NDI_1$ and $NDI_2$ may be penalized in the second term of the above objective function, voxels with NDI below $NDI_1$ or above $NDI_2$ may be ignored. The ellipsis of the second term means that additional NDIVC for the target (or normal tissues) can be specified to have more complete control of the shape of the NDIVH curves. Similar concepts can apply to the NDIVCs which limit the cold spots in the NDIVH curves of the targets that can be useful in specific scenarios.

Any optimization algorithm may be used to adjust from a previous NDIVH to a desired NDIVH, such as limited-memory Broyden-Fletcher-Goldfarb-Shanno (L-BFGS). The optimization algorithm may be deployed through any suitable platforms, such as being integrated in a well-benchmarked open source C++ optimizer package, OPT++, or another system, to solve the treatment planning model. NDIVC method may be based on conventional quadratic programming that is easier to integrate into current commercial treatment planning systems, such as Eclipse™ (Varian Medical Systems, Pal Alto, CA). In some configurations, the problem is not quadratic or convex. Therefore some algorithms, such as L-BFGS, may not be guaranteed to converge to the global minimum. In such cases, a "trial-and-error" process may be used for the treatment planners to make sure that a clinically reasonable plan is achieved and meets all the clinical requirements. During this optimization, the uncertainty scenario to be chosen per voxel may be based on which uncertainty scenario leads to the worst-case dose per voxel. For each iteration during the optimization, the objective function value and the corresponding gradient of the objective function based on the chosen uncertainty scenario may be calculated per voxel and then an algorithm, such as L-BFGS and the like, may be used to derive the updated optimization solution.

Previous methods have been based on multiple criteria optimization (MCO) or linear programming. The MCO framework required a database of pre-computed anchor plans to approximate the Pareto surface. Numerous optimizations would have been needed to generate a database for MCO. The extensive computation requirements would be a significant obstacle for this to be implemented routinely in the clinic. As IMPT has a much larger number of optimization variables than intensity-modulated radiation therapy (IMRT) due to the additional dimension of particle energies, usually much longer computation and optimization times are required. In addition, the implementation of the MCO method is based on the linear projection solver, while a NDIVC method may be based on a conventional quadratic programming, which is easier to integrate into current commercial treatment planning systems, such as the popular Eclipse™ software (Varian Medical Systems, Palo Alto, CA). No clinic with commercial treatment planning system has implemented this MCO optimization algorithm for IMPT. On the other hand, in the linear programming, it only constrains the tail mean dose value (thus suffers from inaccuracies), and the slow computing speed makes it impractical for routine clinic use (it takes up to several days to generate a clinically acceptable plan using linear programming). In addition, the use of linear programming is difficult to be integrated in certain commercial treatment planning systems such as Varian Eclipse™ (Varian Medical Systems, Palo Alto, CA).

In some configurations, the NDIVH-based robust optimization can be performed in a single step and in a way that preserves accuracy. NDIVH optimization can adjust plan robustness of the resulting IMPT plans by applying NDIVC to shape the NDIVH curves. Adjusting the parameters of NDIVC can result in plans with different levels of plan robustness.

In some configurations, the NDIVH curves of two plans intersect with each other. When this occurs, it may be left to the user, such as the physicians and physicists, to choose the appropriate plan in a patient-specific manner, especially when the competing plans have similar NDIVH AUC values.

Figure 4:
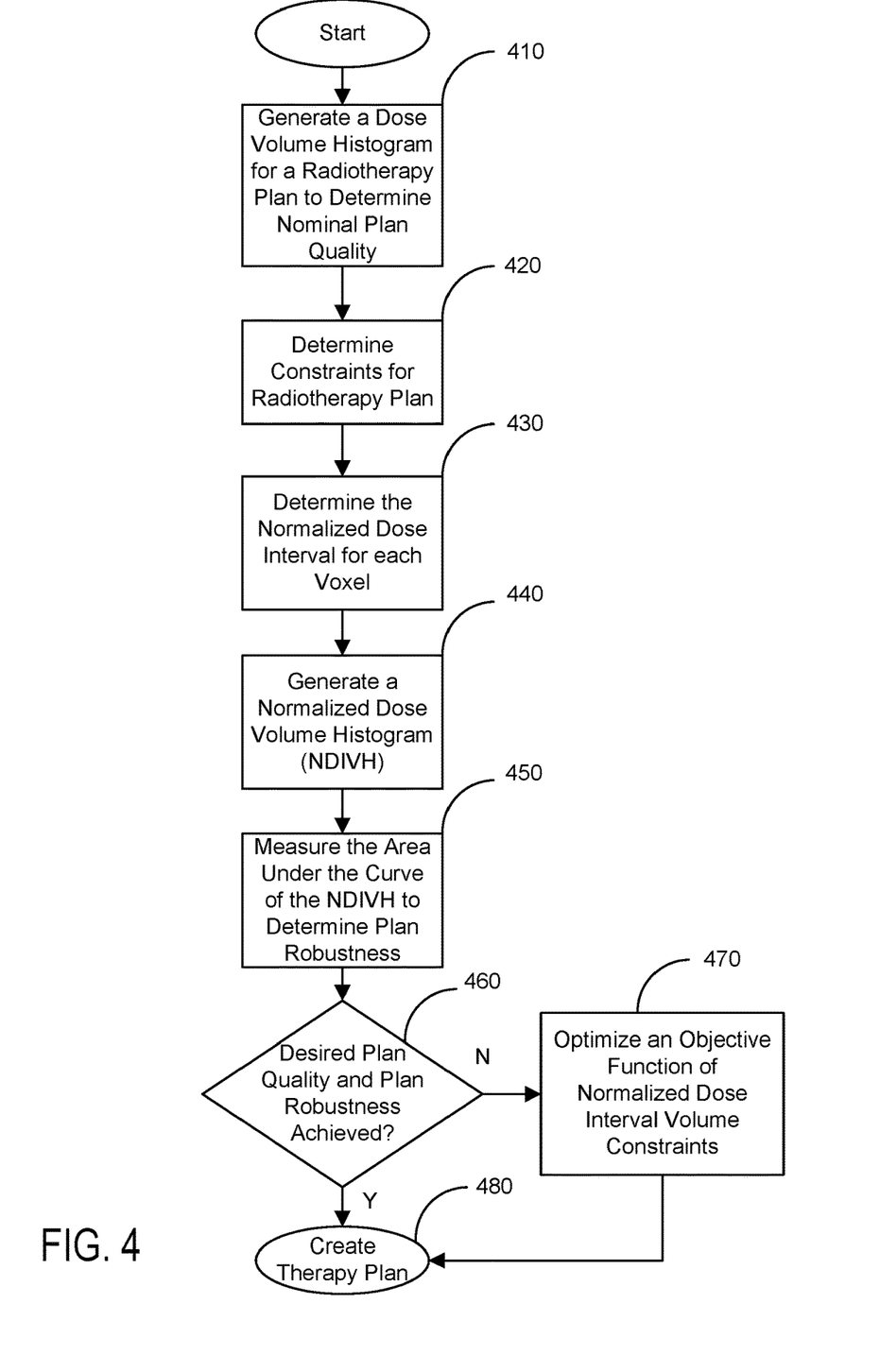
FIG. 4 is a flowchart for one configuration for generating a plan based on NDIVH.
Figure 5A:
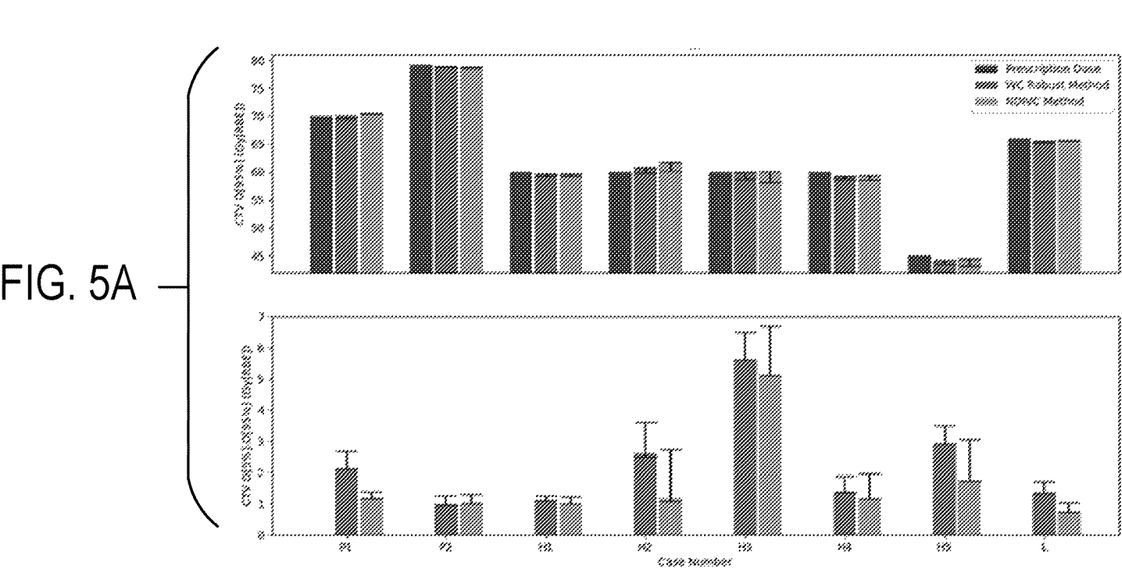
FIGS. 5A-5E depict bar graphs of statistics of a non-limiting example comparison of the DVH indices between a worst-case robust optimization and a NDIVH-based robust optimization applied to eight example clinical cases.
Figure 5B:
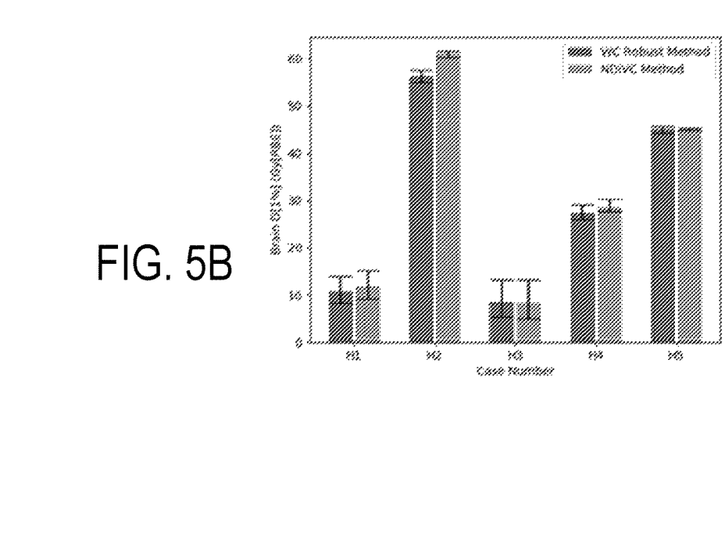
Figure 5C:
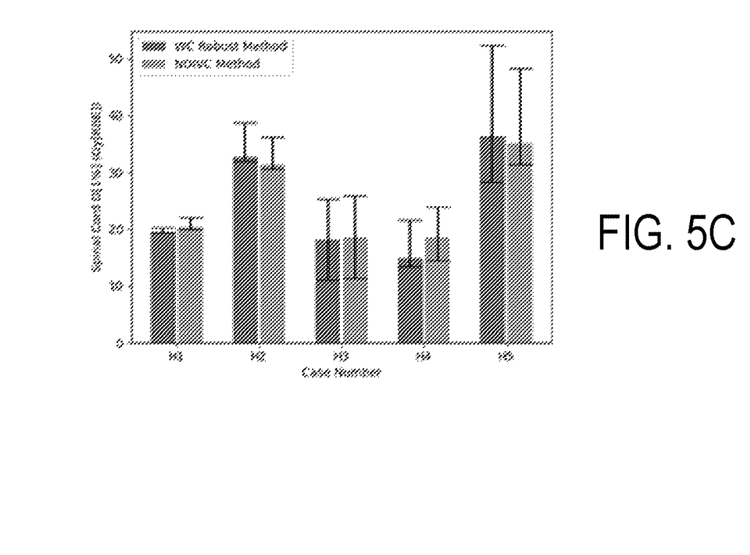
Figure 5D:
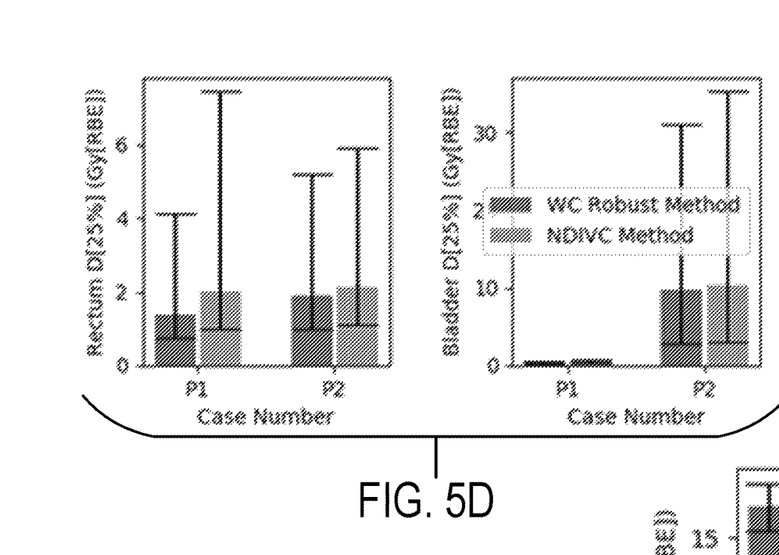
Figure 5E:
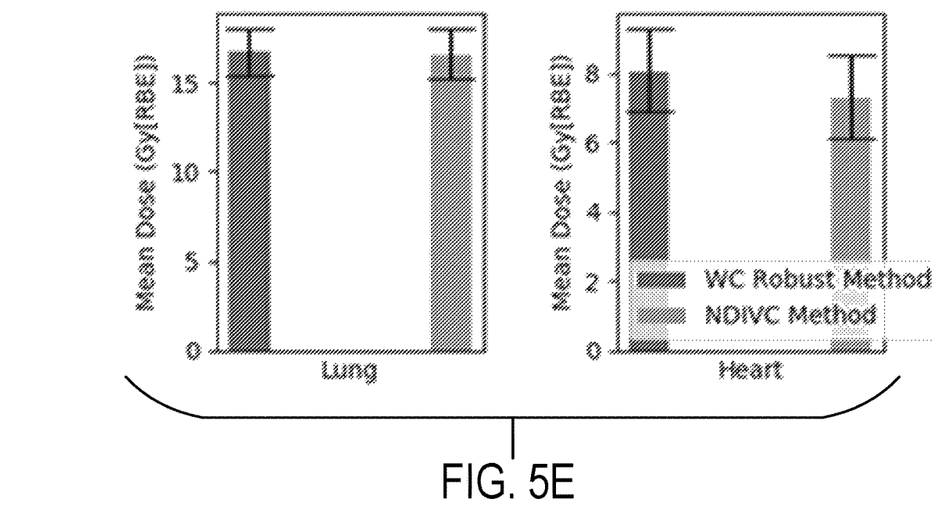

Referring to FIG. 4, a flowchart is shown for one configuration for generating an IMPT plan robust in the face of uncertainties using a NDIVH-based robust optimization method. A dose volume histogram may be generated at step 410 for a radiotherapy plan to assess nominal plan quality. At step 420, constraints for a desired radiotherapy plan are determined, or set up. Constraints may include thresholds or values for plan robustness and plan quality including target dose coverage, target dose homogeneity, and normal tissue protection usually prescribed as dose volume constraints for targets and normal tissues by physicians. Patient setup and proton beam range uncertainties and other parameters, or any combination of parameters may be set up for the optimization. The normalized dose interval for each voxel in a normal organ region of interest (ROI) and/or radiotherapy target regions may be determined at step 430. A normalized dose interval volume histogram (NDIVH) may then be generated at step 440. The area under the curve of the NDIVH may be measured at step 450 in order to assess plan robustness. If the desired balance between nominal plan quality and plan robustness is not met at step 460, then an objective function, such as the function disclosed in equations 2 and 3, may be minimized or optimized in order to meet the desired balance between nominal plan quality and plan robustness. The optimized radiotherapy plan is then generated at step 480.

In one non-limiting example of an NDIVH-based robust optimization, 9 dose distributions corresponding to one nominal and 8 multiple extreme scenarios induced by patient setup and proton beam range uncertainties were derived. The NDIVH-based robust optimization has been benchmarked in an example patient cohort. The example patient cohort includes 1 lung case, 5 head and neck (H&N) cases, and 2 prostate cases and the results were compared to those derived from the voxel-wise worst-case robust optimization. IMPT plans were retrospectively generated for the aforementioned eight clinical cases. Two plans were generated for each patient with the same dosimetric goals and physics characteristics of spots: one from the voxel-wise worst-case robust optimization and the other from the NDIVH-based robust optimization. Nominal plan quality and plan robustness was compared between the two plans. The initial spot arrangements were the same for both methods, including spot position, spot initial intensity, spot energy, and spot spacing for fair comparison. Plans were normalized to have the same mean dose of targets for fair comparison.

The following dosimetric parameters were used to compare nominal plan quality and plan robustness: the dose that covers 95% of the ROI ($D_{95\%}$); the dose that covers 25% of the ROI ($D_{25\%}$); the dose that covers 5% of the ROI ($D_{5\%}$); the dose that covers 1% of the ROI ($D_{1\%}$); and the mean dose. Table 1 includes patient prescriptions, target volumes, and beam angles:

TABLE 1

| Case Number | Tumor Type | Prescription Dose (Gy[RBE]) | Target Volume (cm³) | Beam angles (gantry, couch) | | | |
|---|---|---|---|---|---|---|---|
| | | | | Field 1 | Field 2 | Field 3 | Field 4 |
| P1 | Prostate | 70 | 37.87 | 90°, 0° | 90°, 180° | | |
| P2 | Prostate | 79.2 | 31.14 | 90°, 0° | 90°, 180° | | |
| H1 | H&N | 60 | 106.34 | 65°, 0° | 60°, 180° | | |
| H2 | H&N | 60 | 255.72 | 0°, 0° | 90°, 0° | | |
| H3 | H&N | 60 | 194.25 | 75°, 180° | 75°, 0° | 90°, 270° | 180°, 270° |
| H4 | H&N | 60 | 193.25 | 90°, 270° | 180°, 180° | 34°, 180° | 46°, 180° |
| H5 | H&N | 45 | 93.43 | 60°, 180° | 135°, 180° | 70°, 270° | |
| L | Lung | 66 | 623.61 | 40°, 180° | 130°, 180° | 180°, 180° | |

In the voxel-wise worst-case robust optimization (WC), 9 typical extreme uncertainty scenarios were considered: for setup uncertainties, the iso-center of the patient CTs is shifted by a certain distance in 6 directions of the Cartesian coordinates, and for range uncertainties, the relative stopping power ratio is changed by ±3.5% to model minimum/maximum range uncertainty scenarios, and one nominal scenario. The worst-case dose per voxel is defined as the smallest dose per voxel in the CTV among all doses corresponding to different uncertainty scenarios, while the largest dose per voxel outside the CTV among all doses corresponding to different uncertainty scenarios. The worst dose distribution is used in the optimization as in the following formula:

$$F_{WC}(\vec{\omega}) = \sum_{i \in CTV} p_{CTV,min}(D_{i,min} - D_{0,CTV})^2 + \sum_{i \in CTV} p_{CTV,max}(D_{i,max} - D_{0,CTV})^2 + \sum_{i \in OARs} p_{OARs} \cdot H(D_{i,max} - D_{0,OARs})(D_{i,max} - D_{0,OARs})^2$$

Where $F_{WC}$ is the objective function value of the WC (the voxel-wise worst-case robust optimization) method. p represents the penalty weight of the corresponding term and $D_0$ denotes the prescribed dose for the corresponding region of interest (ROI). The Heaviside function, $H(D_i - D_0)$, is defined conventionally (i.e., its value is unity if $D_i > D_0$ but zero if $D_i \leq D_0$). The terms $D_{i,min} = \min_m(D_i^m)$ and $D_{i,max} = \max_m(D_i^m)$ respectively indicate the minimum and maximum dose among the possible doses $D_i^m$ in voxel i (m=1 ... 9, is the index of the corresponding uncertainty scenario with setup and range uncertainties considered), which are calculated using $D_i^m = \Sigma_j k_{i,j}^m \omega_j^2$ cod in each iteration. The non-negative $\omega_j^2$ is the intensity of j-th beamlet and the influence matrix $k_{i,j}^m$ is defined as the dose contribution of beamlet j with unit weight to voxel i in the uncertainty scenario m. The mth influence matrix $k_{i,j}^m$ incorporates range and setup uncertainties.

Referring to FIGS. 5A-5E, the statistics of a non-limiting example comparison of the DVH indices between the two methods applied to the eight clinical cases are summarized. In general, the NDIVC method achieved better or equal target coverage (higher in CTV $D_{95\%}$) for 7 out of total 8 cases in nominal scenario compared to the WC method. The NDIVC method achieved better target homogeneity (CTV $D_{5\%}$-$D_{95\%}$) in nominal scenario in 7 out of 8 cases. The NDIVC method achieved better or equal protection (lower in the corresponding DVH indices) in 7 out of 16 critical organs demonstrated. In terms of DVH band widths, the NDIVC method achieved smaller or equal robustness band width in 17 out of 32 cases.

Figure 6A:
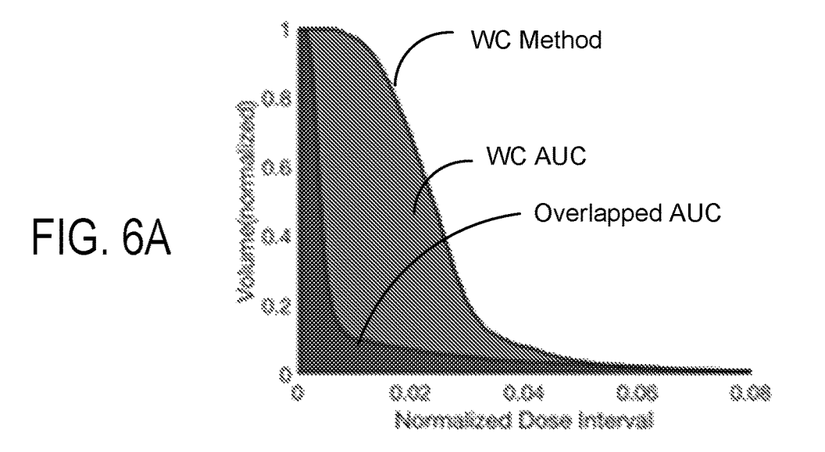
FIG. 6A is a graph of a non-limiting example NDIVH comparison of example plans generated by two methods: (1) a worst-case robust optimization and (2) a NDIVH-based robust optimization for one example prostate case.
Figure 6B:
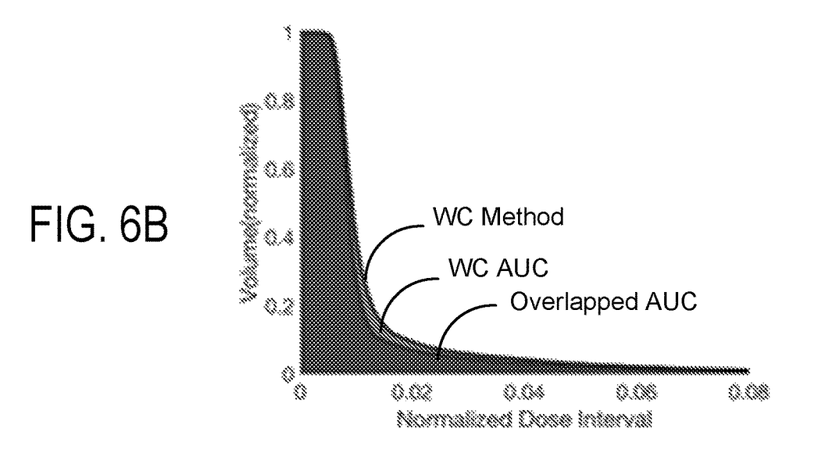
FIG. 6B is a graph of a non-limiting example NDIVH comparison of example plans generated by two methods: (1) a worst-case robust optimization and (2) a NDIVH-based robust optimization for one example head and neck case.
Figure 6C:
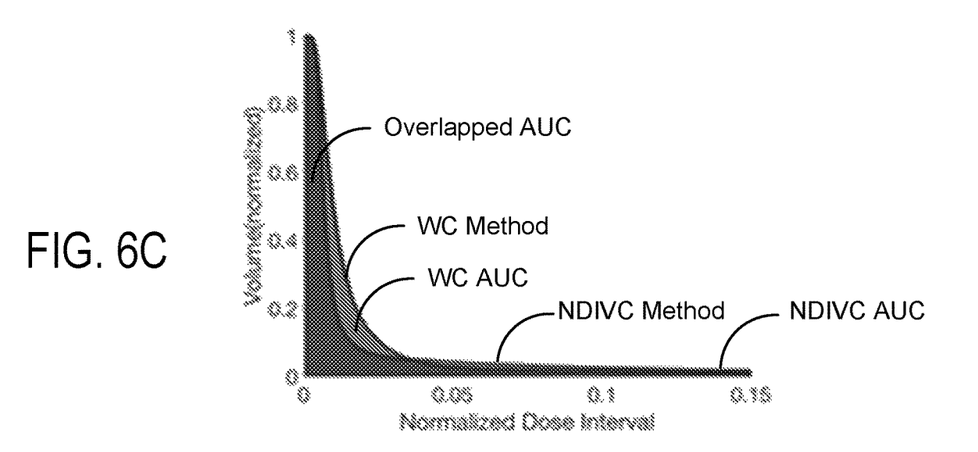
FIG. 6C is a graph of a non-limiting example NDIVH comparison of example plans generated by two methods: (1) a worst-case robust optimization and (2) a NDIVH-based robust optimization for one example lung case.

Referring to FIGS. 6A-C, non-limiting example NDIVH comparisons for one prostate case, one H&N case and the lung case are shown. The comparison of the NDIVH AUCs, which represent plan robustness, of the NDIVC method vs. AUCs of the WC method was 0.0073 vs. 0.0264, 0.0112 vs. 0.0127, and 0.0153 vs. 0.0166, respectively. For the prostate and the H&N case, the NDIVHs of the NDIVC method were always below those of the WC method, while for the lung case, the NDIVH curve of the NDIVC method crossed the NDIVH curve of the WC method (lower in the low NDI region while higher in the high NDI region).

Figure 7:
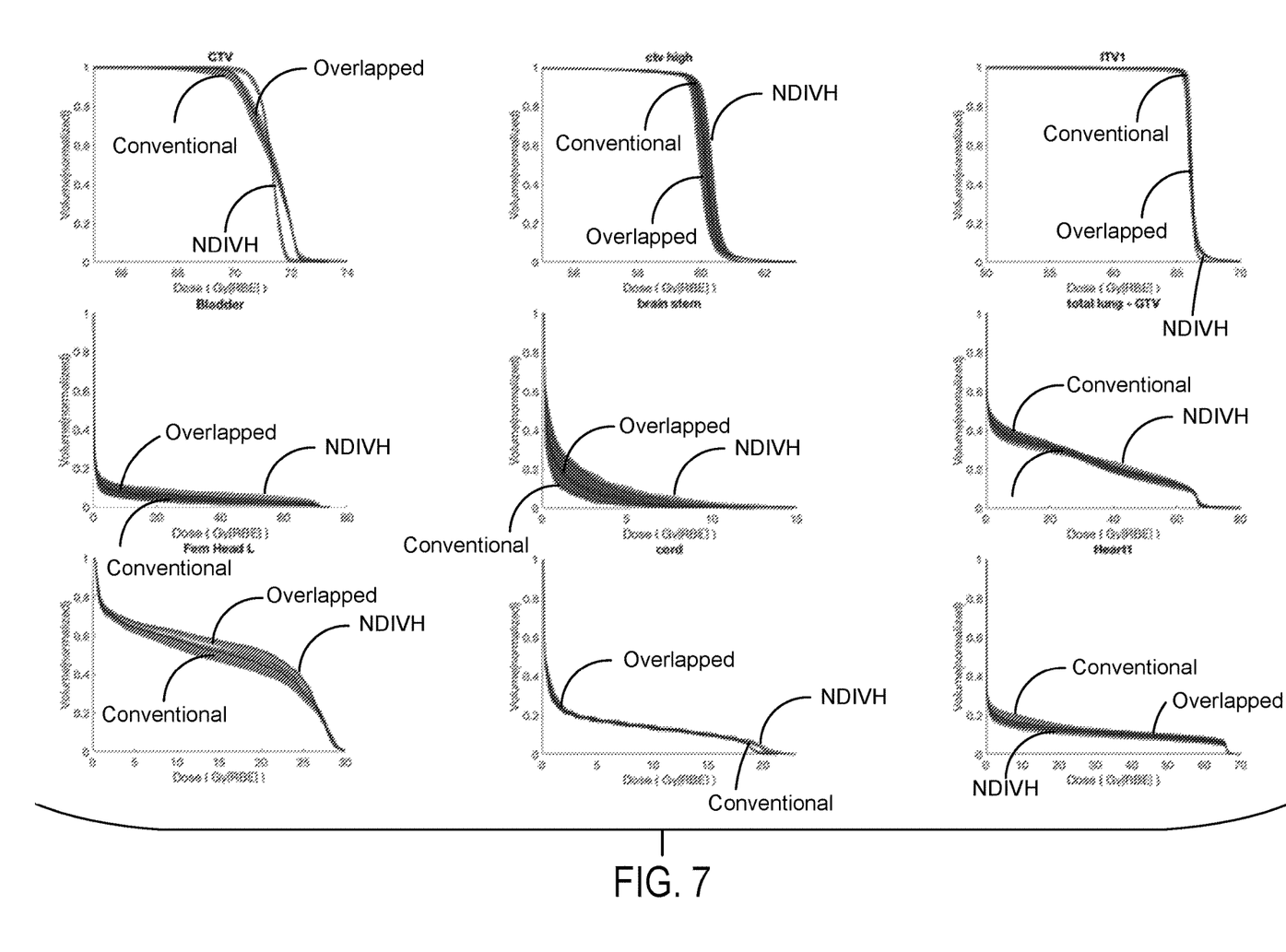
FIG. 7 shows a non-limiting example comparison of example plans derived by two methods: (1) a worst-case robust optimization and (2) a NDIVH-based robust optimization in terms of nominal plan quality and plan robustness using a DVH band method for three example cases.

Referring to FIG. 7, to compare plan robustness and nominal plan quality for the three cases between the two methods discussed above, the bands of the DVH method for the target and some critical organs are shown. The NDIVH method achieved better nominal plan quality (fewer cold spots and fewer hot spots) and plan robustness (thinner DVH band) for the target (top panel). In some cases for the right column, the NDIVH method resulted in more cold spots but fewer hot spots in the target with comparable normal tissue protection. The comparison of plan robustness evaluated by DVH band was consistent with that evaluated by the NDIVH AUC in these cases.

Figure 8A:
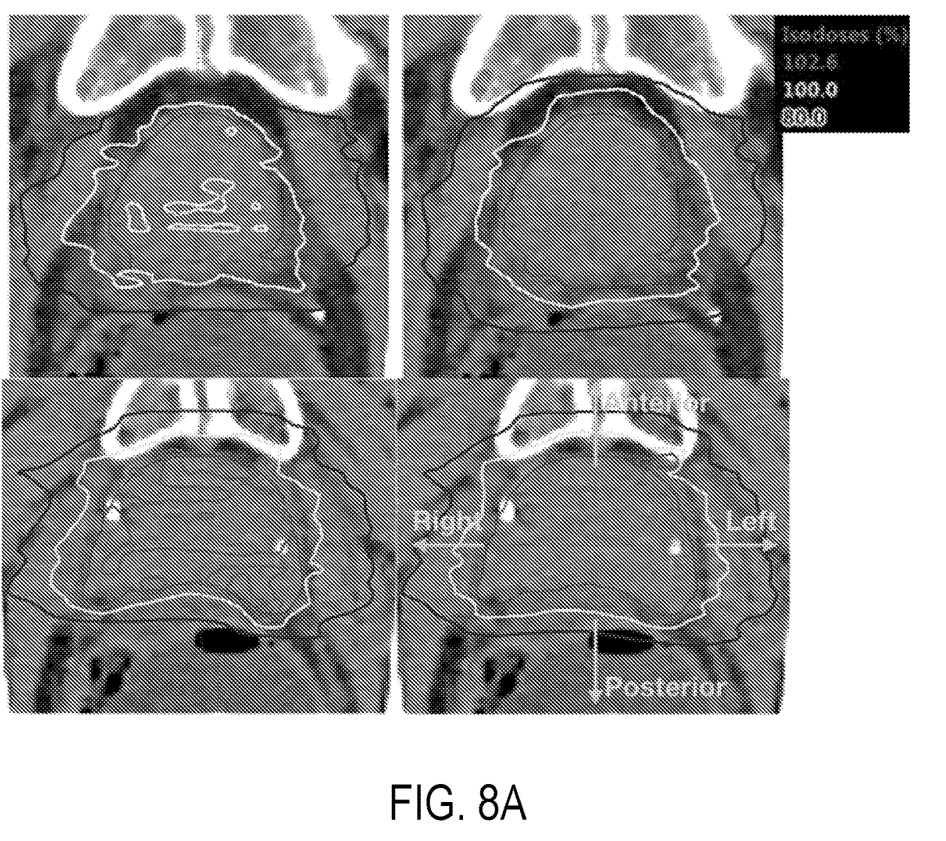
FIG. 8A shows a non-limiting example comparison of transverse dose distributions derived by two methods: (1) a worst-case robust optimization and (2) a NDIVH-based robust optimization at two example CT slices for an example prostate case are shown.

Referring to FIG. 8A, the transverse dose distributions at two typical CT slices for a non-limiting example prostate case are shown. Isodose lines at two typical CT slices are shown to compare the cold spots (top row) and hot spots (bottom row) in the plans derived from the worst-case robust optimization (left panels) and the NDIVH-based robust optimization (right panels), respectively. The different isodose lines normalized to the prescription dose lines are shown. The NDIVH-based robust optimization (right) achieved a more conformal dose distribution with better homogeneity in the target.

Figure 8B:
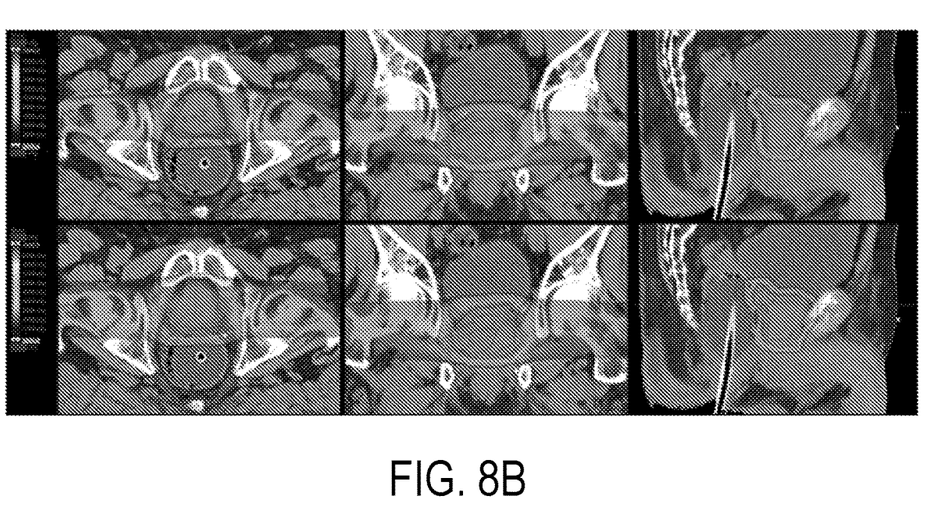
FIG. 8B shows a non-limiting example comparison of example dose distributions at transverse, coronal, and sagittal views between the worst-case (top) and the proposed NDIVH-based (bottom) robust optimization methods.

Referring to FIG. 8B, a non-limiting example comparison of dose color washes at transverse, coronal, and sagittal views between the worst-case robust optimization (top) and the proposed NDIVH-based robust optimization (bottom) for the same prostate cancer patient shown in FIG. 8A are shown. The outer contour line is the CTV.

A performance comparison between the NDIVC method and the conventional voxel-wise worst-case robust method is shown in Table 2 for the 8 example patient cases.

TABLE 2

| Patient No. | Time used in optimization (sec) | |
|---|---|---|
| | NDIVC | WC robust |
| P1 | 413 | 678 |
| P2 | 1079 | 555 |
| H1 | 17082 | 16050 |
| H2 | 641 | 2510 |
| H3 | 19979 | 34242 |
| H4 | 837 | 7693 |
| H5 | 1909 | 1562 |
| L | 21146 | 65446 |

Figure 9:
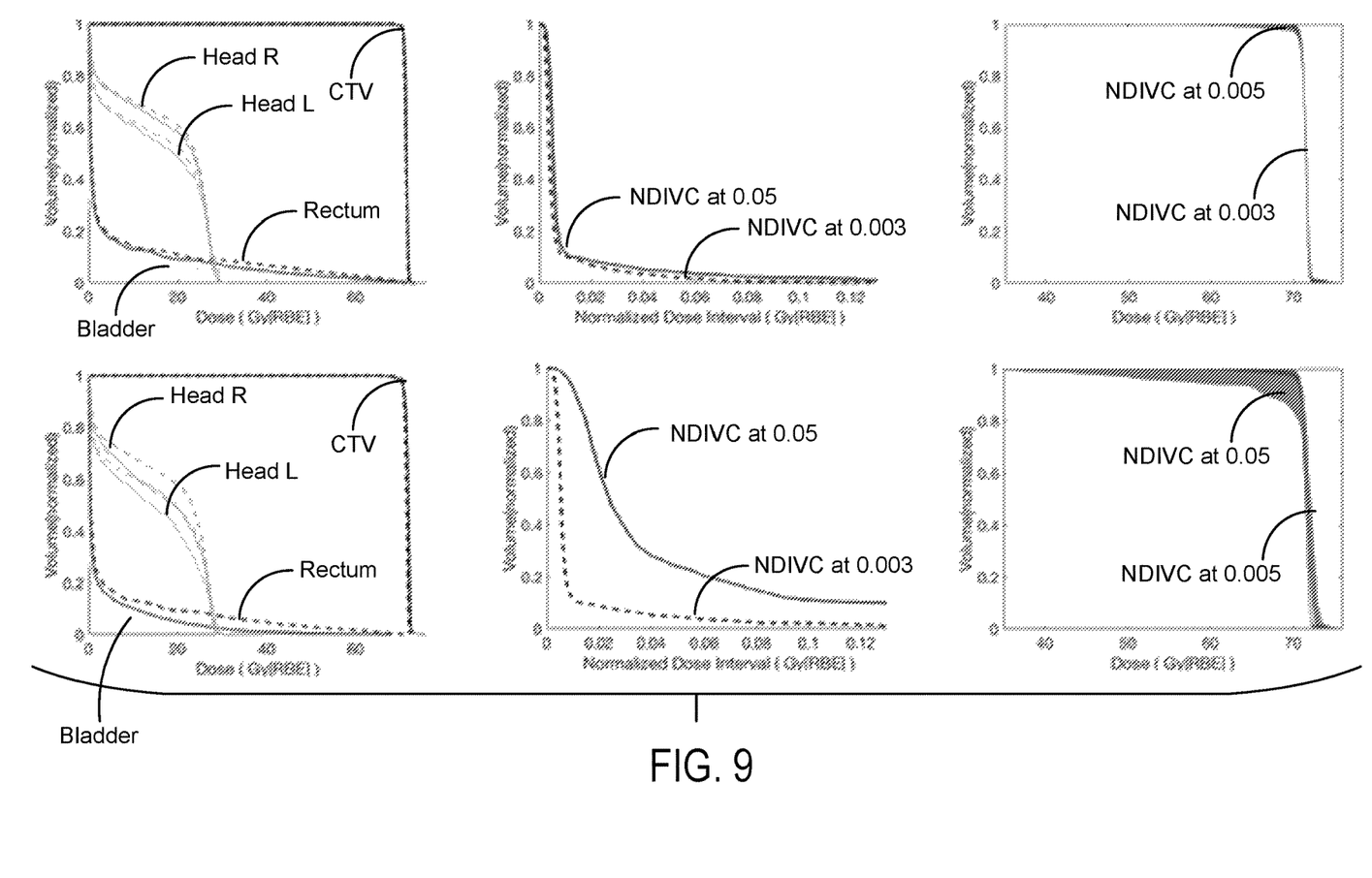
FIG. 9 shows non-limiting example comparisons of plan robustness and nominal plan quality in IMPT planning for an example prostate case, as generated by the NDIVH-based robust optimization under various NDIVC parameters.

Referring to FIG. 9, non-limiting example comparisons of the plan robustness and nominal plan quality of the IMPT plans for an example prostate case generated by the NDIVH-based robust optimization with different NDIVC parameters are shown. The NDVIC was applied to the target only. The nominal plan quality may be assessed by comparing the DVHs of targets and normal tissues in the nominal scenario between the two methods (left panels). The plan robustness may be assessed by comparing the NDIVHs of the target between the two methods (middle), while the plan robustness may also be assessed by comparing the DVH bands of the target to confirm the conclusions (right panels). The top row compared the results from a NDIVC of (0.003, 0.1) with a NDIVC of (0.005, 0.1); the bottom row compared the results from a NDIVC of (0.005, 0.1) with a NDIVC of (0.05, 0.1). The values in the brackets indicate the horizontal and vertical position of the NDIVC in the NDIVH plot of the target. FIG. 9 shows that when loosening the NDIVC constraint, the plan protects normal organs better. In the example shown, all of four mean doses of critical organs: bladder, rectum, femur head left, and femur head right, decreased (from 4.06 Gy[RBE] to 3.53 Gy[RBE] for bladder; from 6.46 Gy[RBE] to 5.42 Gy[RBE] for rectum; from 15.84 Gy[RBE] to 15.28 Gy[RBE] for femur head left; from 17.82 Gy[RBE] to 17.33 Gy[RBE] for femur head right) in the comparison shown in the top row and all decreased (from 3.53 Gy[RBE] to 2.27 Gy[RBE] for bladder; from 5.42 Gy[RBE] to 3.20 Gy[RBE] for rectum; from 15.28 Gy[RBE] to 13.62 Gy[RBE] for femur head left; from 17.33 Gy[RBE] to 15.53 Gy[RBE] for femur head right) in the comparison shown in the bottom row.

The present disclosure has described one or more preferred embodiments, and it should be appreciated that many equivalents, alternatives, variations, and modifications, aside from those expressly stated, are possible and within the scope of the invention.

The invention claimed is:

1. A method for balancing radiation therapy plan robustness and nominal plan quality, comprising:
   a) determining constraints for a radiotherapy plan quality;
   b) calculating normalized dose interval for a plurality of voxels in at least one normal tissue region of interest (ROI) and at least one target ROI in a subject;
   c) generating a normalized dose interval volume histogram using the normalized dose interval for the plurality of voxels in the at least one normal tissue ROI and the at least one target ROI in the subject;
   d) measuring an area under the normalized dose volume histogram to determine the robustness for the plan; and
   e) generating the radiotherapy plan using the normalized dose interval volume histogram (NDIVH) through the use of the normalized dose interval volume constraints.

2. The method of claim 1, wherein the normalized dose interval are used to control the shape of the dose interval volume histogram.

3. The method of claim 1, wherein the normalized dose intervals (NDI) are determined by: $NDI=(D_{max}-D_{min})/D_{max}$, where $D_{max}$ represents the maximum dose, and $D_{min}$ represents the minimum dose among possible doses corresponding to different setup and range uncertainty scenarios for the plurality of voxels in the at least one normal tissue ROI and the at least one target ROI in the subject.

4. The method of claim 3, wherein the NDI are a 3D distribution in the subject.

5. The method of claim 1, further comprising minimizing an objective function that incorporates the plan quality and the plan robustness to generate the radiotherapy plan.

6. The method of claim 1, further comprising optimizing an objective function that incorporates the plan quality and the plan robustness to generate the radiotherapy plan using the normalized dose interval.

7. The method of claim 1, wherein creating the radiotherapy plan includes adjusting a position of the normalized dose interval in the normalized dose interval volume histogram to balance between nominal plan quality and plan robustness.

8. The method of claim 1, wherein the constraints include at least one of a threshold for plan robustness, a threshold for plan quality including target dose coverage, target dose homogeneity, normal tissue protection value, patient setup uncertainty value, proton beam range uncertainty value, or a combination thereof.

9. The method of claim 1, further comprising generating a dose volume histogram prior to generating a normalized dose interval volume histogram.

10. A system for balancing radiation therapy plan robustness and nominal plan quality, comprising:
    a computer system configured to:
    i) determine constraints for a radiotherapy plan quality;
    ii) calculate normalized dose interval for a plurality of voxels in at least one normal tissue region of interest (ROI) and at least one target ROI in a subject;
    iii) generate a normalized dose interval volume histogram using the normalized dose interval for the plurality of voxels in the at least one normal tissue ROI and the at least one target ROI in the subject;
    iv) measure an area under the normalized dose volume histogram to determine the robustness for the plan; and
    v) generate the radiotherapy plan using the normalized dose interval volume histogram (NDIVH) through the use of the normalized dose interval volume constraints.

11. The system of claim 10, wherein the normalized dose interval are used to control the shape of the dose interval volume histogram.

12. The system of claim 10, wherein the normalized dose intervals (NDI) are determined by: $NDI=(D_{max}-D_{min})/D_{max}$, where $D_{max}$ represents the maximum dose, and $D_{min}$ represents the minimum dose among possible doses corresponding to different setup and range uncertainty scenarios for the plurality of voxels in the at least one normal tissue ROI and the at least one target ROI in the subject.

13. The system of claim 12, wherein the NDI are a 3D distribution in the subject.

14. The system of claim 10, wherein the computer system is further configured to minimize an objective function that incorporates the plan quality and the plan robustness to generate the radiotherapy plan.

15. The system of claim 10 wherein the computer system is further configured to optimize an objective function that incorporates the plan quality and the plan robustness to generate the radiotherapy plan using the normalized dose interval.

16. The system of claim 10, wherein creating the radiotherapy plan includes adjusting a position of the normalized dose interval in the normalized dose interval volume histogram to balance between nominal plan quality and plan robustness.

17. The system of claim 10, wherein the constraints include at least one of a threshold for plan robustness, a threshold for plan quality including target dose coverage, target dose homogeneity, normal tissue protection value, patient setup uncertainty value, proton beam range uncertainty value, or a combination thereof.

18. The system of claim 10, further comprising generating a dose volume histogram prior to generating a normalized dose interval volume histogram.

* * * * *